United States Patent
Jorgenson et al.

(10) Patent No.: US 6,852,074 B1
(45) Date of Patent: Feb. 8, 2005

(54) BIOLOGICAL PROCESSING APPARATUS FOR EXPRESSING FLUID MATERIAL

(75) Inventors: Glen Jorgenson, Marlboro, MA (US); Donald Barry, Norwood, MA (US); Bruce H. Edwards, Marlboro, MA (US); John P. O'Brien, Brighton, MA (US); Victor Sacco, Jr., Revere, MA (US)

(73) Assignee: ZymeQuest, Inc., Beverly, MA (US)

( * ) Notice: Subject to any disclaimer, the term of this patent is extended or adjusted under 35 U.S.C. 154(b) by 0 days.

(21) Appl. No.: 09/082,200

(22) Filed: May 20, 1998

Related U.S. Application Data
(60) Provisional application No. 60/047,213, filed on May 20, 1997.

(51) Int. Cl.[7] .......................... B04B 11/00; B04B 15/02
(52) U.S. Cl. .............................. 494/13; 494/27; 494/45
(58) Field of Search ........................ 494/13–14, 23–30, 494/35, 42, 45, 47, 48, 81

(56) References Cited

U.S. PATENT DOCUMENTS

| | | | |
|---|---|---|---|
| 3,244,362 A | * | 4/1966 | Hein ............................ 494/30 |
| 3,244,363 A | * | 4/1966 | Hein |
| 3,326,458 A | * | 6/1967 | Meryman et al. |
| 3,456,875 A | * | 7/1969 | Hein |
| 3,489,145 A | | 1/1970 | Judson et al. |
| 3,565,330 A | | 2/1971 | Latham, Jr. |
| 3,737,096 A | | 6/1973 | Jones et al. |
| 3,987,961 A | * | 10/1976 | Sinn et al. |
| 4,300,717 A | | 11/1981 | Latham, Jr. |
| 4,387,848 A | | 6/1983 | Kellogg et al. |
| 4,767,396 A | | 8/1988 | Powers |
| 5,045,048 A | | 9/1991 | Kaleskas et al. |
| 5,114,396 A | * | 5/1992 | Unger et al. |
| 5,318,512 A | | 6/1994 | Neumann |
| 5,356,365 A | * | 10/1994 | Brierton ....................... 494/14 |
| 5,368,542 A | * | 11/1994 | McMannis et al. ........... 494/45 |
| 5,386,734 A | | 2/1995 | Pusinelli |
| 5,651,766 A | * | 7/1997 | Kingsley et al. ........... 604/6.04 |
| 5,676,644 A | | 10/1997 | Toavs et al. |
| 5,733,253 A | * | 3/1998 | Headley et al. ................ 604/4 |
| 6,007,509 A | * | 12/1999 | Kingsley et al. ........... 604/6.02 |
| 6,019,742 A | * | 2/2000 | Headley et al. .............. 494/26 |
| 6,039,711 A | * | 3/2000 | Headley et al. .............. 494/26 |
| 6,074,335 A | * | 6/2000 | Headley et al. .............. 494/47 |
| 6,099,491 A | * | 8/2000 | Headley et al. .............. 494/10 |
| 6,175,420 B1 | * | 1/2001 | Barry et al. |
| 6,296,602 B1 | * | 10/2001 | Headley ....................... 494/37 |
| 6,425,414 B2 | * | 7/2002 | Jorgensen et al. |
| 6,439,577 B2 | * | 8/2002 | Jorgensen et al. |
| 6,558,307 B2 | * | 5/2003 | Headley ....................... 494/37 |
| 6,602,179 B1 | * | 8/2003 | Headley et al. .............. 494/41 |

FOREIGN PATENT DOCUMENTS

EP    0 682 953 A1    11/1995
WO    96/28199        9/1996

OTHER PUBLICATIONS

Perry, Robert H. Perry's Chemical Engineer's Handbook, 6th ed. McGraw–Hill. pp. 22–4 and 22–5, 1984.*

* cited by examiner

*Primary Examiner*—Charles E. Cooley
(74) *Attorney, Agent, or Firm*—Mintz, Levin, Cohn, Ferris, Glovsky and Popeo, P.C.

(57) ABSTRACT

A method and apparatus for selectively expressing one or more selected fluid materials out of a fluid container, including a centrifuge rotor having a round centrifuge chamber of selected volume, a round expandable enclosure disposed within the centrifuge chamber having a rotation axis coincident with the central rotation axis and a flexible wall, a pump for controllably pumping a selected volume of expresser fluid into and out of the expandable enclosure wherein the fluid container is receivable within the centrifuge chamber, and a retaining mechanism for holding the fluid container within the centrifuge chamber in a coaxial position. The flexible wall of the fluid container is in contact with the flexible wall of the expandable enclosure.

37 Claims, 14 Drawing Sheets

FIG. 9
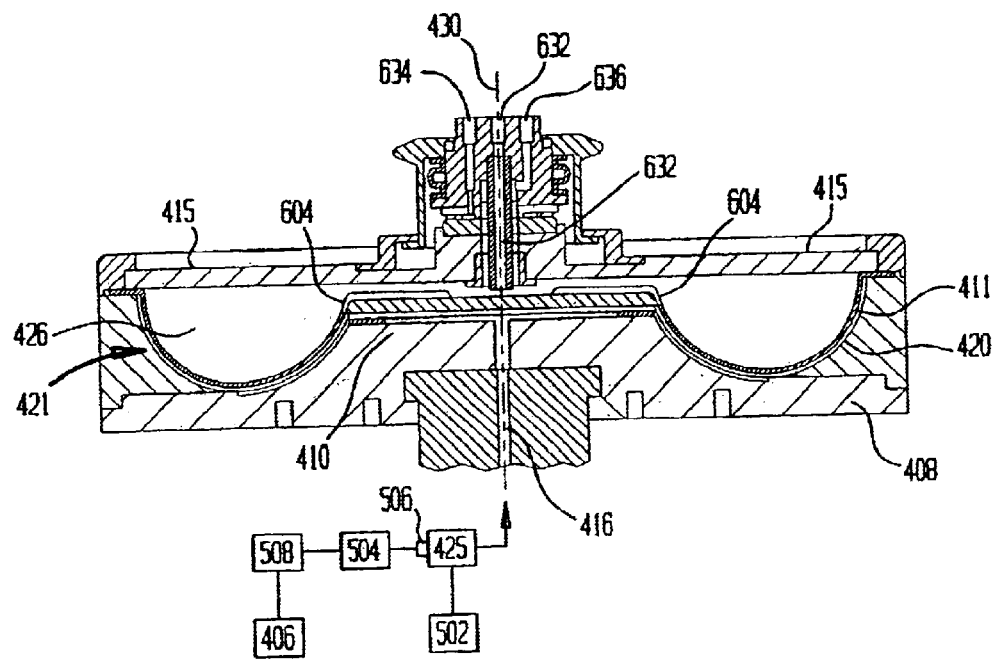
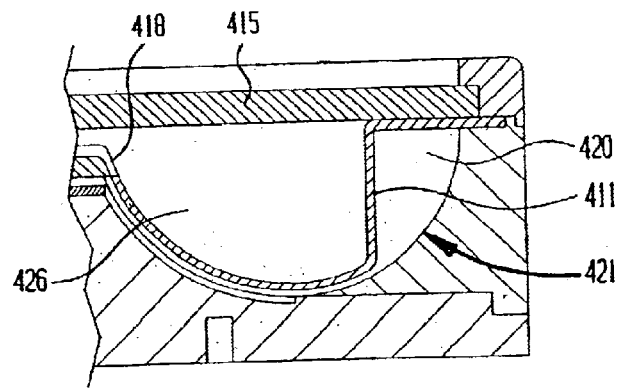
FIG. 10
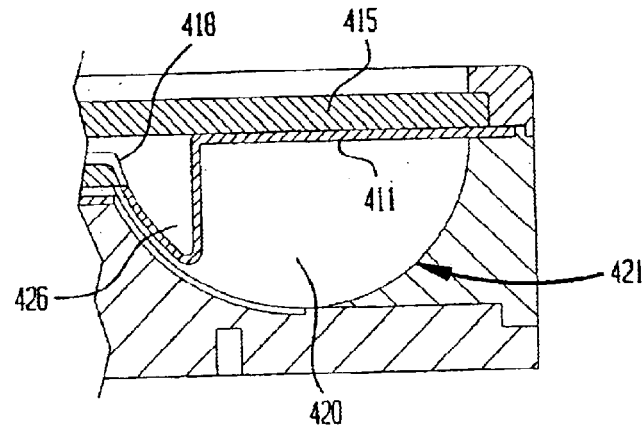
FIG. 11

BIOLOGICAL PROCESSING APPARATUS FOR EXPRESSING FLUID MATERIAL

RELATED APPLICATIONS

This application claims the benefit under Title 35, U.S.C. § 119(e) of pending U.S. Provisional Application Ser. No. 60/047,213, filed May 20, 1997, entitled "Cell Processing System", incorporated herein by reference. This application is also related to co-pending U.S. patent applications entitled: "Rotating Seals for Cell Processing Systems" (U.S. Application Ser. No. 09/081,733 filed May 20, 1998, now abandoned); "Fluid Management Systems" (U.S. Application Ser. No. 09/082,200 filed May 20, 1998): "Optical Sensors for Cell Processing System," (U.S. Pat. No. 6,175,420); and "Cell Processing Systems" (U.S. Application Ser. No. 09/082,341filed May 20, 1998, now abandoned), the disclosures of all of which are incorporated by reference.

BACKGROUND

In order to prepare cells for transfusion or transplantation, it may be necessary to process the cells using an operation, which removes unwanted chemical and/or cellular elements. For example, in preparing frozen erythrocytes for transfusion, erythrocytes are separated from cryopreservatives and other blood components, such as white blood cells, platelets, and subcellular debris. It is important that cell processing be performed under conditions which minimize the risk of microbial contamination.

Further where cell (such as eukaryotic cells, bacteria, or yeast) are cultured in bioreactors for the synthesis of pharmaceuticals, it is necessary to separate the cells from their culture medium.

A number of devices and techniques have been developed to process cells for the foregoing purposes, as described, for example, in European Patent No. 00575858/EP B1 by Witthaus Et al. And U.S. Pat. No. 4,919,817 by Schoendorfer and Williamson, and other patents as set forth below.

Generally, cell processing requires steps in which cells or cell elements are separate from a liquid phase. This separation is typically accomplished by centrifugation.

Also as part of the separation process, a number of devices have been developed which incorporate a means of expressing (i.e., promoting the exit) fluid which has been removed from harvested cells. Disclosures relating to expression include U.S. Pat. No. 4,332,351 by Kellogg and Druger, U.S. Pat. No. 4,010,894 by Kellogg and Kruger, U.S. Pat. No. 4,007,871 by Jones and Kellogg, U.S. Pat. No. 3,737,097 by Jones et al., EP 00265795/EP B1 by Polaschegg, U.S. Pat. No. 4,934,995 by Cullis, U.S. Pat. No. 4,223,672 by Terman et al., and U.S. Pat. No. 4,213,561 by Bayham.

The present invention relates to biological fluid and/or cell processing apparatus and, more particularly, to an apparatus for separating fluid materials having different densities from each other, most typically in a centrifugal field, or otherwise such as in a gravitational field. More particularly, the present invention relates to an apparatus designed to add additional fluids to wash or otherwise treat one or more of the cellular components after the less dense fractions of the solution have been separated and expressed from, or pushed out of, the centrifugal (or gravitational) field. Automated systems for processing cellular material in this manner have typically relied on inefficient centrifugal containment devices and complex fluid management hardware to remove the separated fractions from the centrifuge chamber. Sterility, temperature control, ratio of volume of input fluids, ability to process variable volumes and simplification of the mechanisms used for expressing materials out of a cell or fluid processing chamber are concerns that have been addressed in a variety of inefficient or expensive apparatus and methods in the past.

SUMMARY OF THE INVENTION

In accordance with the invention there is provided an apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising, a centrifuge rotor having a round centrifuge chamber of selected volume, the centrifuge rotor being controllably rotatable around a central axis by a motor mechanism; a round expandable enclosure disposed within the centrifuge chamber having a rotation axis coincident with the central rotation axis and a flexible wall, the fluid container having a rotation axis and being coaxially receivable within the centrifuge chamber, the expandable enclosure being sealably connected to a source of an expresser fluid which has a density selected to be greater than the density of each of the selected one or more fluid materials disposed in the fluid container; a pump for controllably pumping a selected volume of the expresser fluid into and out of the expandable enclosure wherein the fluid container is receivable within the centrifuge chamber; a retaining mechanism for holding the fluid container within the centrifuge chamber in a coaxial position wherein the flexible wall of the fluid container is in contact with the flexible wall of the expandable enclosure.

The expandable enclosure preferably comprises a flexible membrane sealably attached to a surface of the rotor such that the centrifuge chamber is divided into a first chamber for receiving the fluid container and a second fluid sealed chamber for receiving the expresser fluid. The flexible wall of the expandable enclosure typically comprises an elastomeric sheet material. The apparatus further typically includes a heater mechanism having a control mechanism for selectively controlling the temperature of the expresser fluid.

Due to its higher density, the expresser fluid which is pumped into the expandable enclosure travels to a circumferential position within the expandable enclosure which is more radially outward from the central axis than a circumferential position to which the one or more selected fluid materials in the fluid container travel when the rotor is drivably rotated around the central axis.

The fluid container typically has a first radius and the second fluid sealed chamber typically has a second radius which is at least equal to the first radius of the fluid container, wherein the expresser fluid which is pumped into the second fluid sealed chamber travels to an outermost circumferential position within the second fluid sealed chamber which is more radially outward from the central axis than a circumferential position to which the one or more selected fluid materials in the fluid container travel when the rotor is drivably rotated around the central axis.

Further, in accordance with the invention, there is provided in a centrifuge apparatus comprising a rotor having a centrifuge chamber which is controllably rotatable around a central axis, a method for expressing one or more selected fluid materials each having a selected density out of a fluid container which contains the selected fluid materials wherein the fluid container comprises a round enclosure having a radius, a rotation axis, a flexible wall and an exit port sealably communicating with the fluid container for enabling the selected fluid materials contained therein to be expressed out of the fluid container through the exit port, the method comprising: forming a round expandable enclosure within the centrifuge chamber wherein the expandable enclosure has a flexible wall, a radius and a rotation axis coincident with the central axis of the rotor; mounting the fluid container coaxially within the centrifuge chamber such that the flexible wall of the fluid container faces the flexible wall of the expandable enclosure; selecting an expresser fluid having a density greater than the density of each of the selected fluid materials; pumping the selected expresser fluid into the expandable enclosure in an amount sufficient to expand the expandable enclosure such that the flexible wall of the expandable enclosure contacts the flexible wall of the fluid container; and, drivably rotating the rotor around the central axis before, during or after the step of pumping.

Further, in accordance with the invention, there is provided an apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising; a separation housing having a round chamber of selected volume, the housing having a central axis; a round expandable enclosure disposed within the round chamber having an axis coincident with the central axis of the separation chamber and a flexible wall, the fluid container having an axis and being coaxially receivable within the round chamber, the expandable enclosure being sealably connected to a source of an expresser fluid which has a density selected to be greater than the density of each of the selected one or more fluid materials disposed in the fluid container; a pump for controllably pumping a selected volume of the expresser fluid into and out of the expandable enclosure wherein the fluid container is receivable within the round chamber; a retaining mechanism for holding the fluid container within the round chamber in a coaxial position wherein the flexible wall of the fluid container is in contact with the flexible wall of the expandable enclosure.

Further, in accordance with the invention, there is provided an apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising: a centrifuge rotor having a round centrifuge chamber of selected volume, the centrifuge rotor being controllably rotatable around a central axis by a motor mechanism; a round expandable enclosure disposed within the centrifuge chamber having a rotation axis coincident with the central rotation axis and a flexible wall, the fluid container having a rotation axis and being coaxially receivable within the centrifuge chamber, the expandable enclosure being sealably connected to a source of an expresser fluid; a pump for controllably pumping a selected volume of the expresser fluid into and out of the expandable enclosure; wherein the fluid container has a flexible wall and is receivable within the centrifuge chamber such that the flexible wall of the fluid container faces the flexible wall of the expandable enclosure; a mechanism for filling the fluid container with any preselected variable volume of the one or more selected fluid materials which is less than the selected volume of the centrifuge chamber; a retaining mechanism for holding the fluid container completely within the centrifuge chamber upon expansion of the expandable enclosure.

Further, in accordance with the invention, there is provided in a centrifuge apparatus comprising a rotor having a centrifuge chamber of a selected volume which is controllably rotatable around a central axis, a method for expressing one or more selected fluid materials each having a selected density out of a fluid container which contains the selected fluid materials wherein the fluid container comprises a round enclosure having a rotation axis, a flexible wall and an exit port sealably communicating with the fluid container for enabling the selected fluid materials contained therein to be expressed out of the fluid container through the exit port, the method comprising: forming a round expandable enclosure within the centrifuge chamber wherein the expandable enclosure has a flexible wall and a rotation axis coincident with the central axis of the rotor; mounting the fluid container coaxially within the centrifuge chamber such that the flexible wall of the fluid container faces the flexible wall of the expandable enclosure; filling the fluid container with any preselected variable volume of the one or more of the selected fluid materials which is less than the selected volume of the centrifuge chamber before, during or after the step of mounting; pumping a selected expresser fluid into the expandable enclosure in an amount sufficient to expand the expandable enclosure such that the flexible wall of the expandable enclosure contacts the flexible wall of the fluid container; holding the fluid container completely within the centrifuge chamber during the step pumping and, drivably rotating the rotor around the central axis before or during the step of pumping.

The step of pumping typically includes preselecting the expresser fluid to have a density greater than the density of each of the selected fluid materials. The method may further comprise placing the expresser fluid at one or more selected temperatures prior to or during the step of pumping.

Further, in accordance with the invention, an apparatus for selectively expressing one or more fluid materials out of a fluid container includes an IR temperature sensor (e.g., an IR thermocouple) for measuring the temperature of the fluid materials located in the fluid container prior to the selective expressing. The apparatus also includes a second expressing temperature sensor for measuring the temperature of the ambient between the fluid container and the IR sensor. Alternatively, the second temperature sensor may be replaced by another means that characterize changes in the refractive index of the infrared radiation emitted from the fluid material in order to correct the IR data.

Further, in accordance with the invention, there is provided a centrifuge apparatus comprising of a rotor having a centrifuge chamber of a selected volume which is controllably rotatable around a central axis, a method for consistently processing a selected biological cell material between separate processing cycles in the centrifuge apparatus, the method comprising: selecting a fluid material having a predetermined composition for treatment of the selected biological cell material; forming a round expandable enclosure within the centrifuge chamber wherein the expandable enclosure has a flexible wall and a rotation axis coincident with the central axis of the rotor; mounting a round fluid container having rotation axis, a flexible wall and an exit port sealably communicating with the fluid container coaxially within the centrifuge chamber such that the flexible wall of the fluid container faces the flexible wall of the expandable enclosure; filling the fluid container with a volume of the selected biological cells and a volume of the selected fluid material in a predetermined ratio before, during or after the step of mounting; pumping a selected expresser fluid into the expandable enclosure in an amount sufficient to expand the expandable enclosure such that the flexible wall of the expandable enclosure contacts the flexible wall of the fluid container; holding the fluid container completely within the centrifuge chamber during the step pumping; drivably rotating the rotor around the central axis before or during the step of pumping; and, repeating the steps of mounting, filling, pumping, holding and drivably rotating at least once.

The heater control mechanism typically includes a program for automatically controlling the temperature of the expresser fluid. The expresser fluid is typically circulated through a reservoir, within which, the fluid is in thermal contact with certain devices that transfer thermal energy to or from the fluid in response to a control algorithm. These thermal devices may include Peltier Devices, electric resistance submersion heaters, air-cooled radiators, or other similar devices or some combination of these types of thermal transfer devices.

BRIEF DESCRIPTION OF THE DRAWINGS

The invention is described with reference to representative examples and embodiments shown in the accompanying drawing wherein:

FIG. 9 is a schematic side cross-sectional view of the FIG. 8 view showing the flexible membrane component 411 seated initially at the beginning of a processing cycle along the curved surface of the bowl or donut shaped separation chamber 421 of chuck 408;

FIG. 10 is a close-up cross-sectional view of a portion of FIG. 9 showing the expresser fluid chamber 420 partially filled with expresser fluid at a later stage in a typical processing cycle;

FIG. 11 is a view of FIG. 10 at an even later stage of a typical processing cycle showing the expresser fluid chamber 42 filled to a greater degree/volume than the chamber is filled in FIG. 10;

DETAILED DESCRIPTION OF CERTAIN EMBODIMENTS

Figure 1:
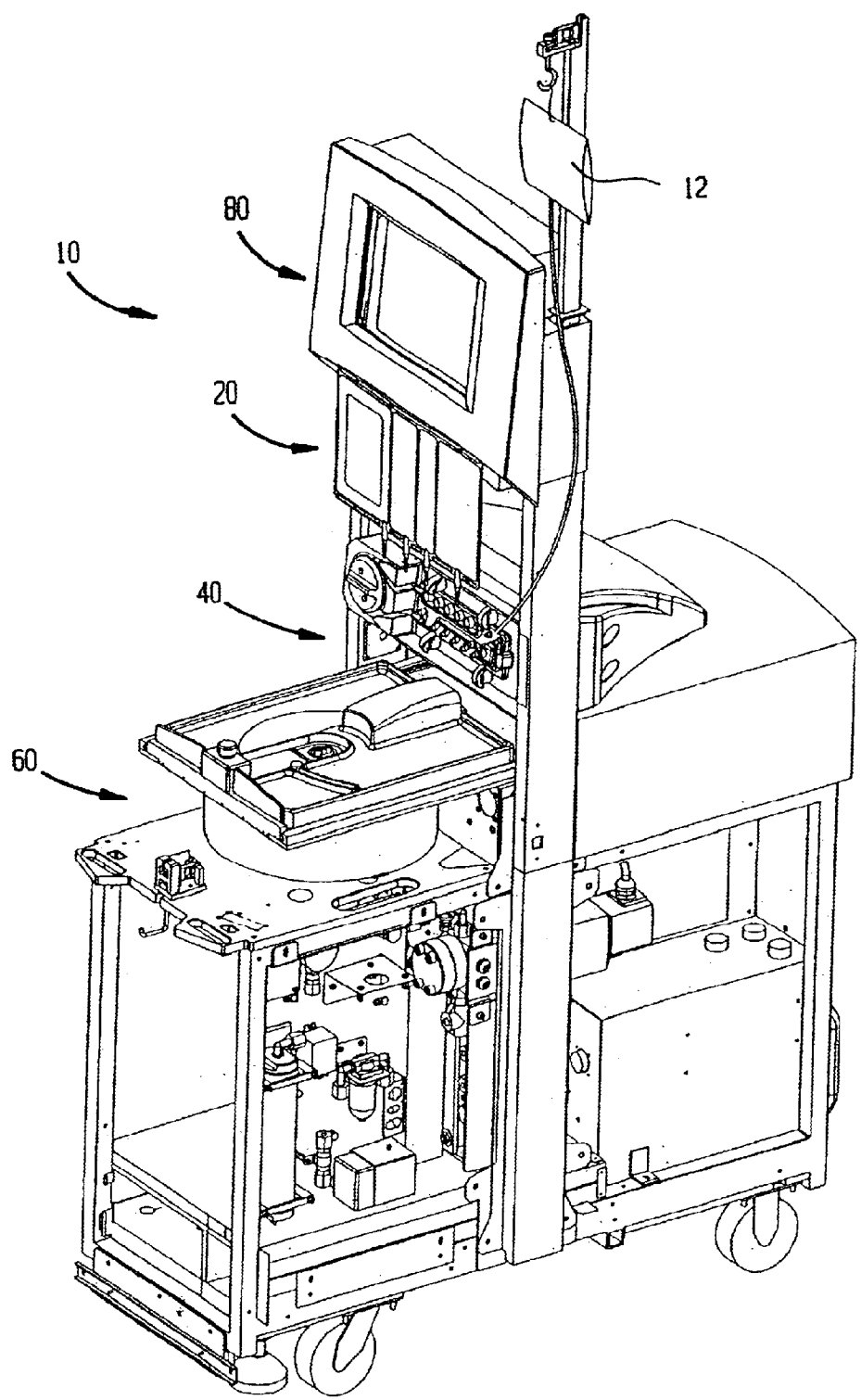
FIG. 1 is a perspective view of an interactive cell processing system.
Figure 3:
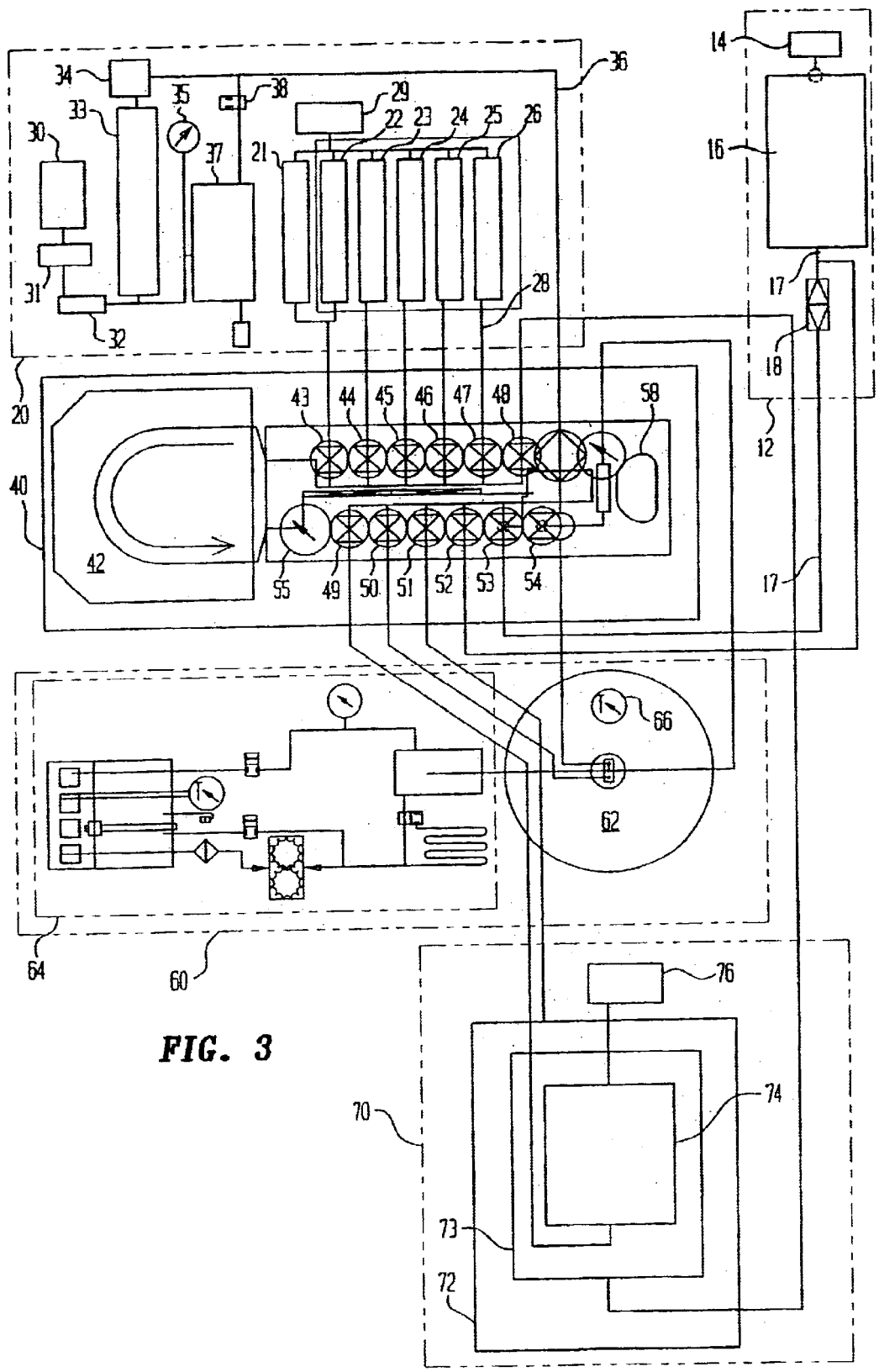
FIG. 3 is a block diagram of the interactive cell processing system of FIG. 1.

Referring to FIGS. 1 and 3, an interactive cell processing system 10 includes a cell module 12, a supply module 20, a fluid distribution module 40, a processing module 60, a collection module 70 (not shown in FIG. 1) and a control module 80. These modules are operatively interconnected for processing biological cells in a sterile environment. Cell module 12 is constructed for short term or long-term storage of biological cells for processing. Supply module 20 includes several containers for storing different process chemicals including saline or other fluids used for processing the cells and/or sterile air, typical processing being the treating of the cells with selected active materials such as enzymes, buffers, and polyethylene glycol (PEG), nucleic acids and the like, washing the cells with selected fluids such as buffers, saline and the like and compacting the cells for purposes of separating them from the suspending media. The containers are connected to fluid distribution module 40 by a set of conduits. Fluid distribution module 40 includes several valves and sensors for dispensing controlled amounts of the process chemicals from supply module 20 to processing module 60 and for dispensing a known amount of the biological cells from cell module 12 to processing module 60. Furthermore, fluid distribution module 40 is constructed to direct the process waste from processing module 60 to a waste container 72 and processed cells to a cell storage container 74, both of which are located in collection module 70, while maintaining the purity and sterility of the cells. Control module 80 directs the entire process according to a selected algorithm.

Figure 2:
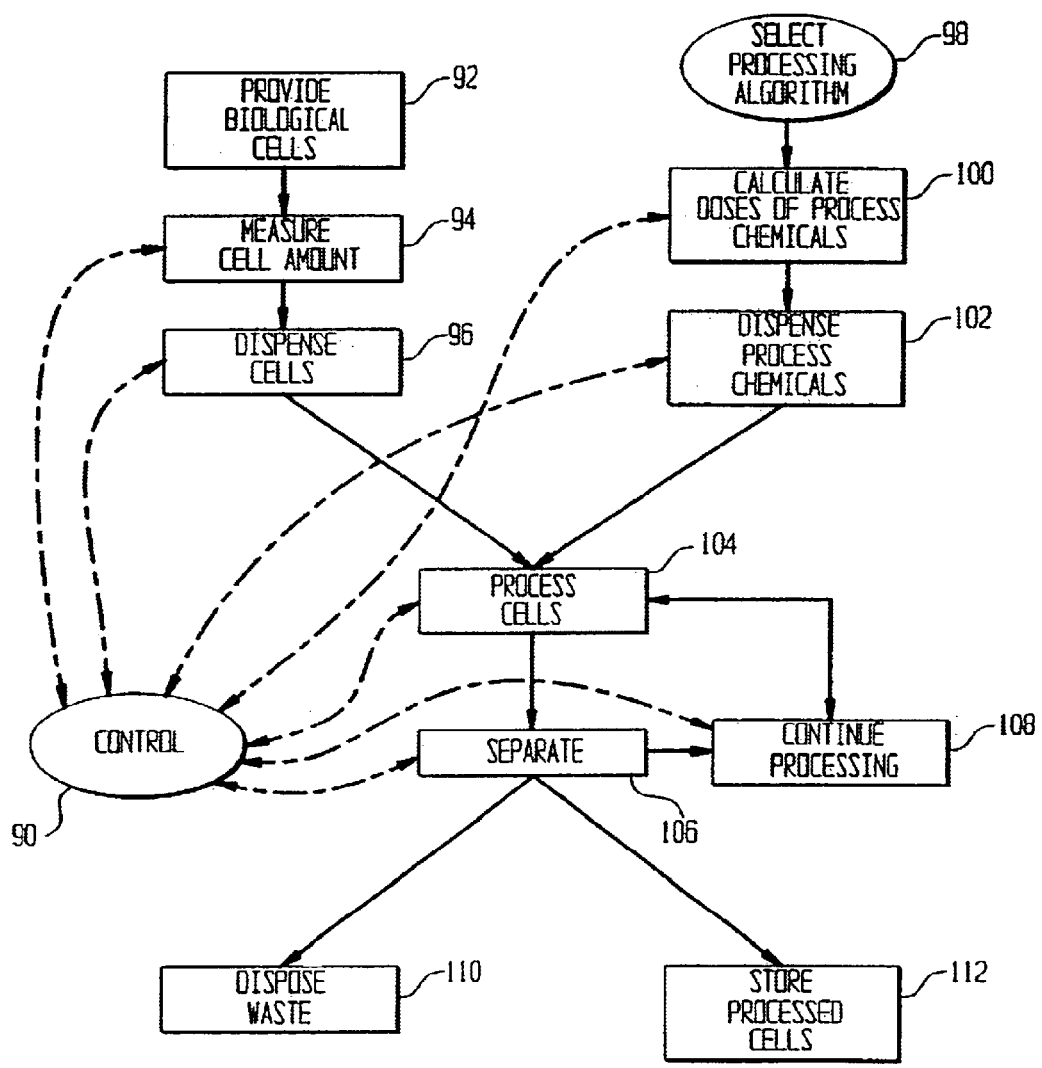
FIG. 2 is a conceptual flow diagram displaying operation of an interactive cell processing system.

In general, the operation of cell processing system 10 is shown in FIG. 2. Control module 80 executes a processing algorithm selected initially 98. Control module 80 includes a logic controller that receives real-time data from several in-line sensors arranged in a processing loop. A mass sensor (or a volume sensor) measures an initial amount of the provided biological cells 94 and sends the data to control module 80. Control module 80 controls the amount of cells dispensed to processing module 60 in accordance with the processing algorithm. Based on the provided amount of the biological cells, control module 80 also calculates the individual doses of the process chemicals 100 and directs a set of control valves to dispense the chemicals 102 in a selected order to processing module 60, again in accordance with the processing algorithm.

Control module 80 executes iteratively the processing algorithm. Control module 80 receives data from the individual sensors (e.g., a weight sensor, a volume sensor, a temperature sensor, an optical sensor, a resistance or capacitance sensor, a flow sensor, a pressure sensor or another sensor arranged to monitor the transferred matter in a liquid, gaseous or solid state). After dispensing the selected amount of one or several processing chemicals to processing module 60, control module 80 regulates the temperature and the time of processing and directs the processing module to agitate, mix or otherwise treat the cells with the process chemicals. Depending on the processing algorithm, control module 80 may manage several processing cycles. At the end of each cycle, processing module 60 may separate the processed cells from intermediate products and from the process waste. During the separation process, fluid distribution module 40 detects the fluid component being expressed from processing module 60 and directs the separated components to different containers for disposal 110 or storage 112. Each processing cycle may use a different processing chemical and different processing conditions. Cell processing system 10 can also process different types of cells at the same time or sequentially. Furthermore, cell processing system 10 may also partially process biological cells and then store them in cell storage container 74 (shown in FIG. 3), which may include a temperature control system. The processed cells may be later automatically dispensed from cell storage container 74 and processed using another processing algorithm. The processed cells may also be grown in culture prior to another use.

Cell processing system 10 may process any collection of cells (such as blood cells) which are fluid enough in mass composition to flow readily through biological fluid delivery tubing, bags and the like.

Referring again to FIG. 3, in one preferred embodiment of the cell processing system, cell module 12 includes a weight sensor 14 arranged to weigh red blood cells provided in a bag 16. Tubing 17 connects a bag 16 to a leuko filter 18 and to fluid distribution module 40. Supply module 20 includes a bag 21 with enzyme A1/B, a bag 22 with enzyme A2, a bag 23 with 140 m Molar Potassium Phosphate DiBasic pH 9.0 (DPP), a bag 24 with PEG (polyethylene glycol), a bag 25 with storage solution, and a bag 26 with Phosphate Citrate Isotonic (PCI). Each bag is connected by tubing 28 to fluid distribution module 40. A weight sensor 29 is constructed to weigh any of the above-mentioned fluids located in supply module 20. Supply module 20 also includes a compressor 30 connected via a filter 31 and a check valve 32 to air reservoir 33, which stores sterile air used for cell processing. Pressure switch and sensor 34 is in communication with air tubing 36, which delivers sterile air to an air filter located in fluid distribution module 40. A regulator 37 connected to a solenoid valve 36 regulates the air pressure provided to fluid distribution module 40 and to processing module 60. Fluid distribution module 40 includes a peristaltic pump 42 and twelve plunger valves 43 through 54 connected to a set of conduits for distributing the processed chemicals and the cells during the automated process. A pressure sensor 55 measures the fluid pressure during the process, and an optical detector 58 monitors the fluid to and from processing module 60.

Processing module 60 preferably includes a centrifuge or sedimentation or gravity/separation chamber apparatus 62 and an expressor fluid system 64. An IR temperature sensor 66 monitors the temperature of the processed chemicals or the cells located inside the centrifuge 62. Collection module 70 includes a waste bag 72, a saline solution bag 74, and a product bag 76. Collection module 70 also includes a weight sensor 76 connected to product bag 74 and arranged to weigh the processed red blood cells. Specifically, the logic controller received input from:

the weight of the initial and final blood bags,
the weight of the processing fluids,
the temperature of the blood and the expressing fluid,
and the pressure of the fluid upstream from the sterilizing filter and the rotating seal as well as the pressure of the expressing fluid and the sterile air supply.

Based on a programmed algorithm, the controller sends output signals to:

the processing and expresser pumps,
the temperature controller (heating and cooling), typically a controller for heating and/or cooling the expressor fluid;
and any combination of the twelve valves.

Figure 4:
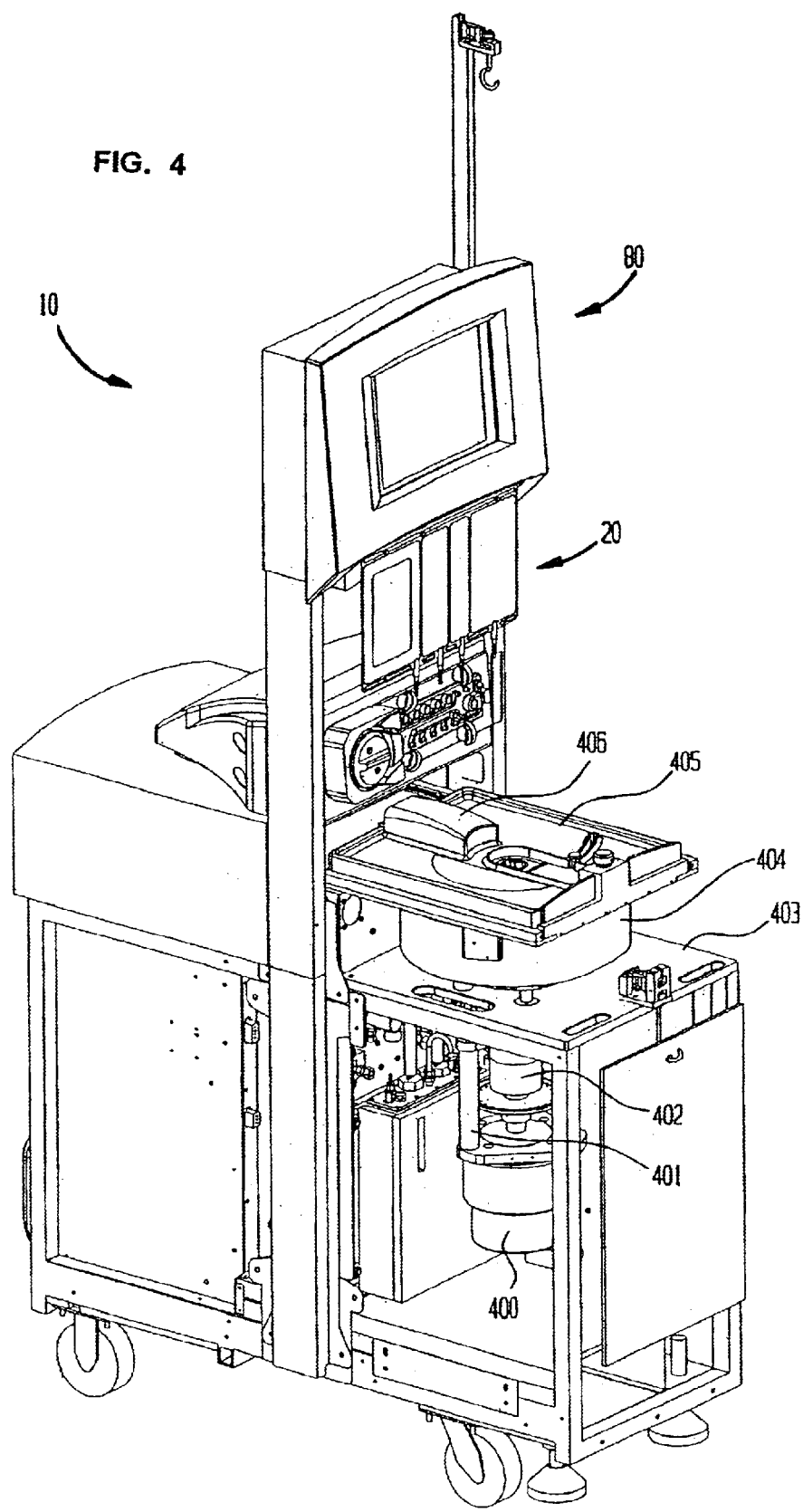
FIG. 4 is a left side perspective view of the FIG. 1 system.

FIG. 4 shows the FIG. 1 apparatus 10 in a left side perspective view showing the expressor system components more clearly in assembled and mounted relationship relative to the overall apparatus 10.

In particular, a motor 400 for rotatably driving a chuck or rotor (described in detail below), separation posts 401, bearing housing 402, mounting plate 403, bucket 404, a sliding cover 405 and an infrared sensor housing assembly 406 are shown in FIG. 4.

Figure 12:
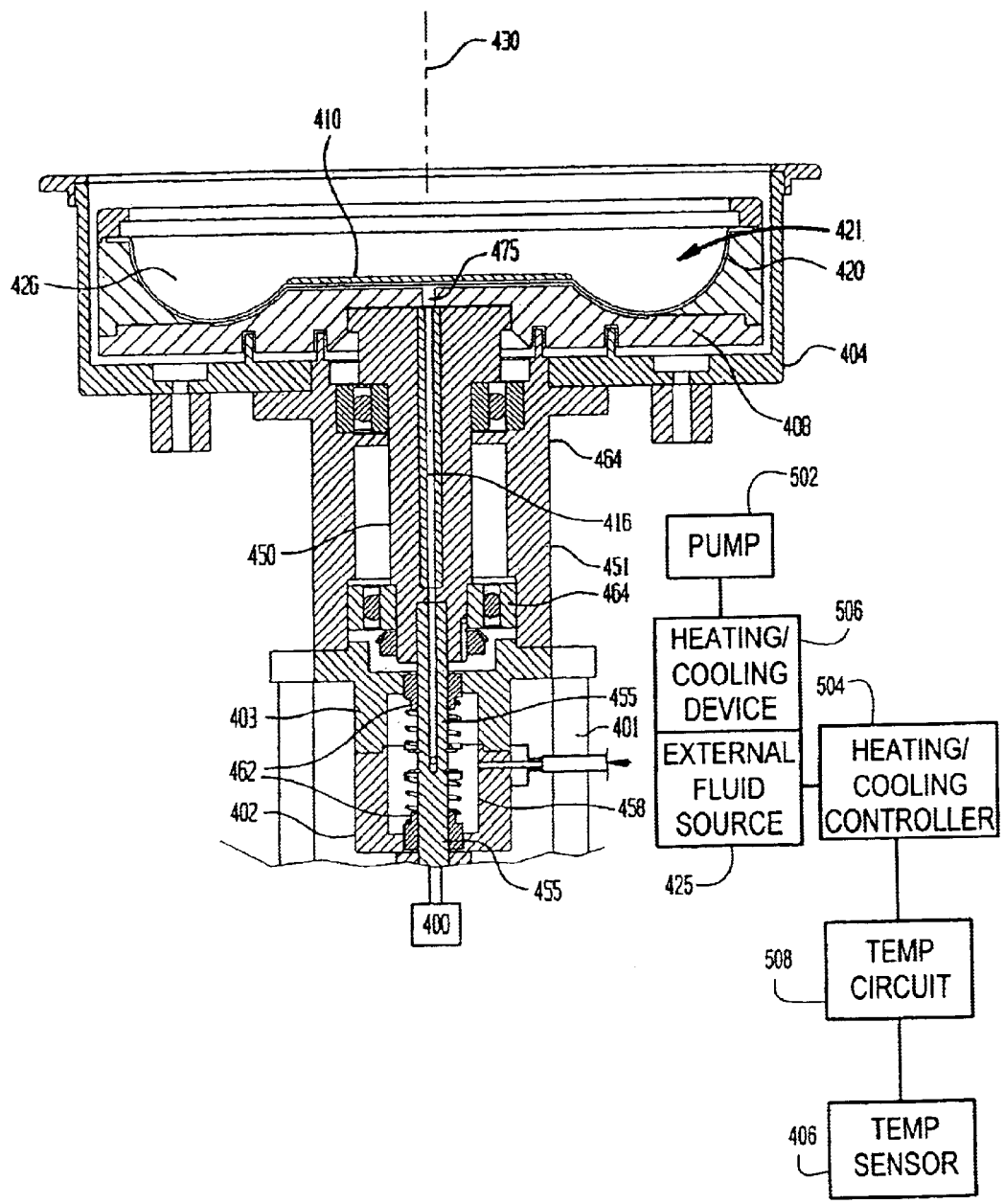
FIG. 12 is another schematic side cross-sectional view of the expresser system subassembly of FIGS. 4–11 showing additional components by which expresser fluid is input from a pumping source through a central drive shaft which is rotatably driven.
Figure 13:
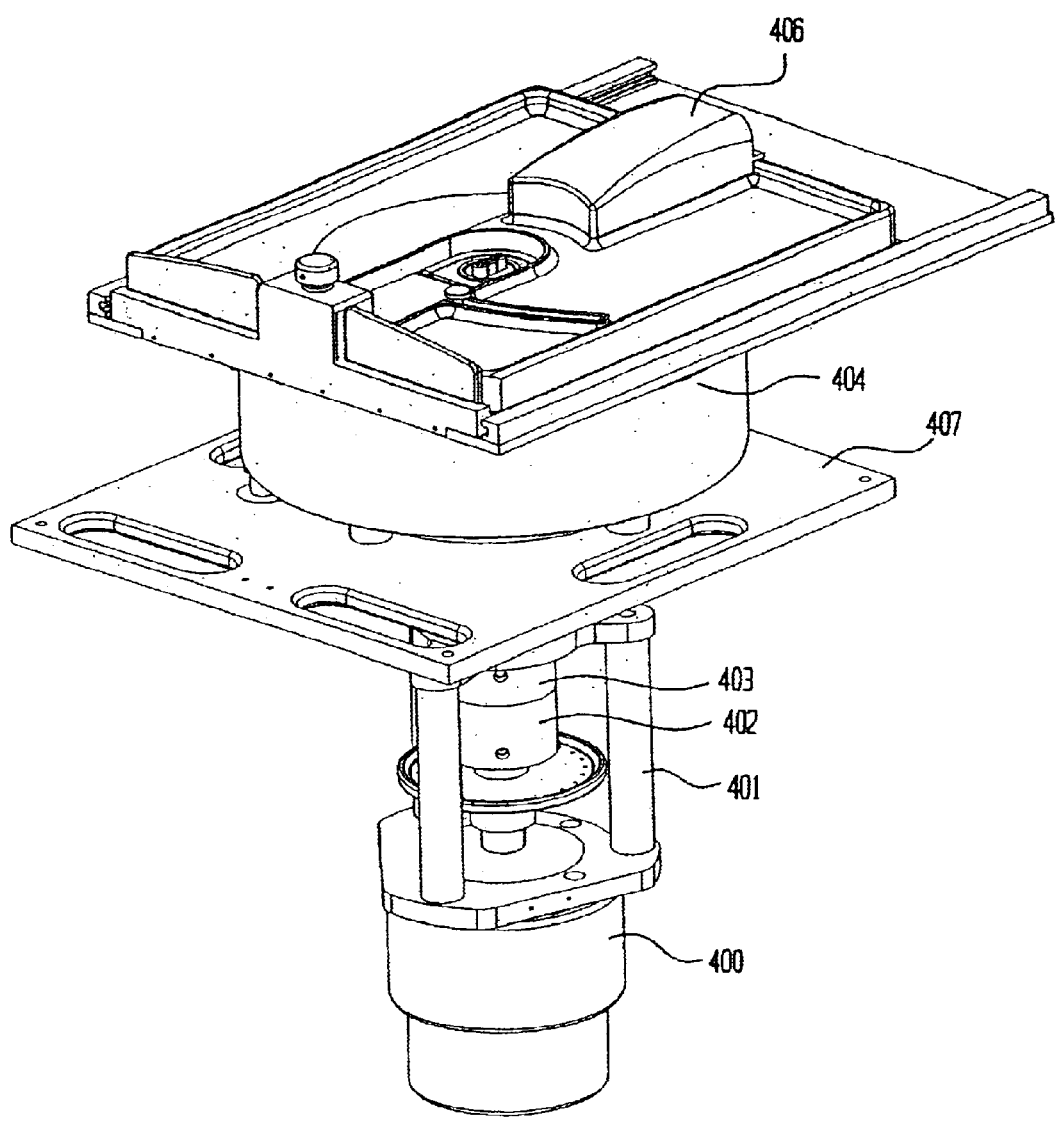
FIG. 13 is an isometric view of the FIG. 5 components in assembled form.
Figure 14:
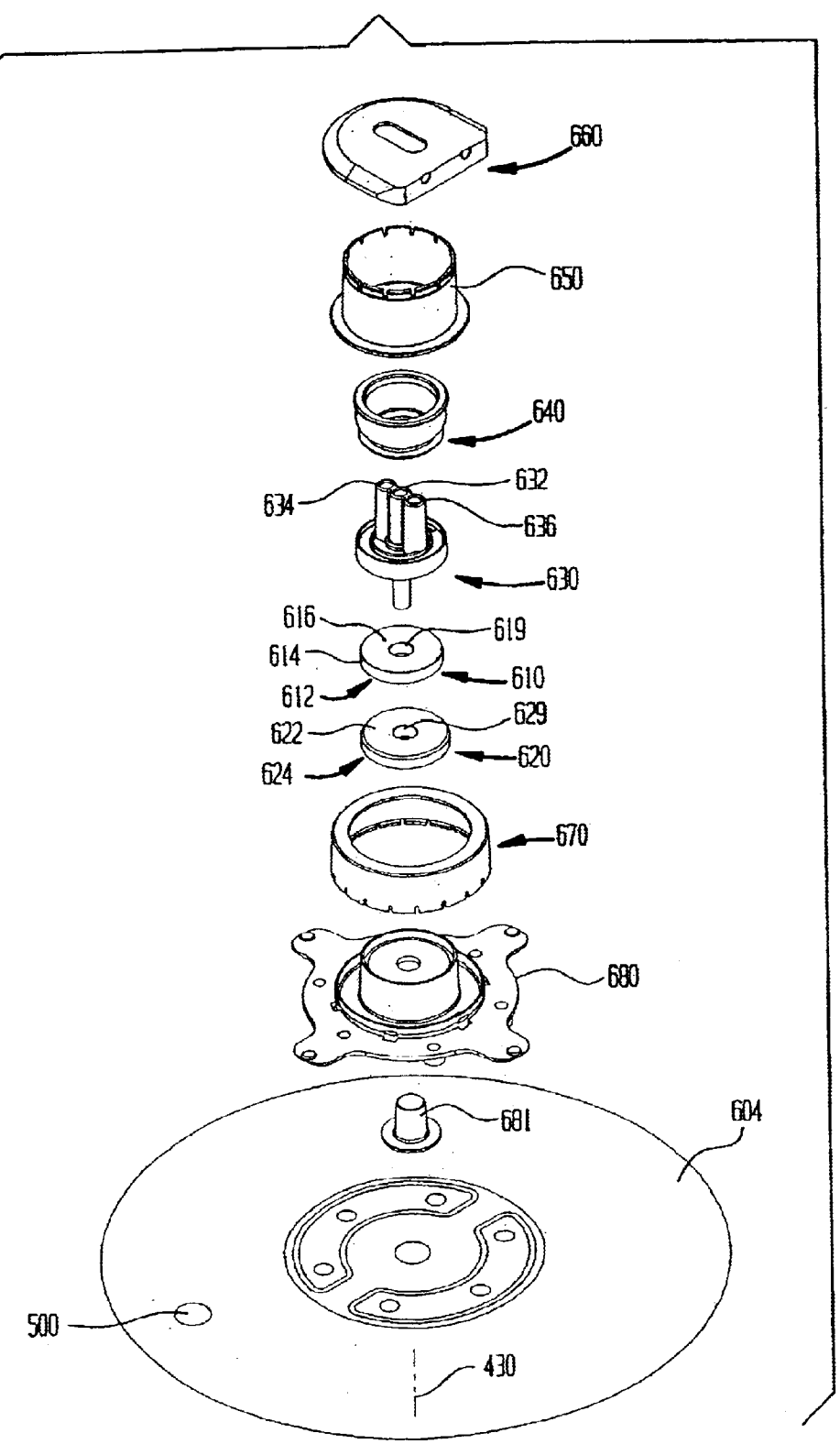
FIG. 14 is an exploded isometric view of a rotating seal used in conjunction with an expresser system of the invention.
Figure 15:
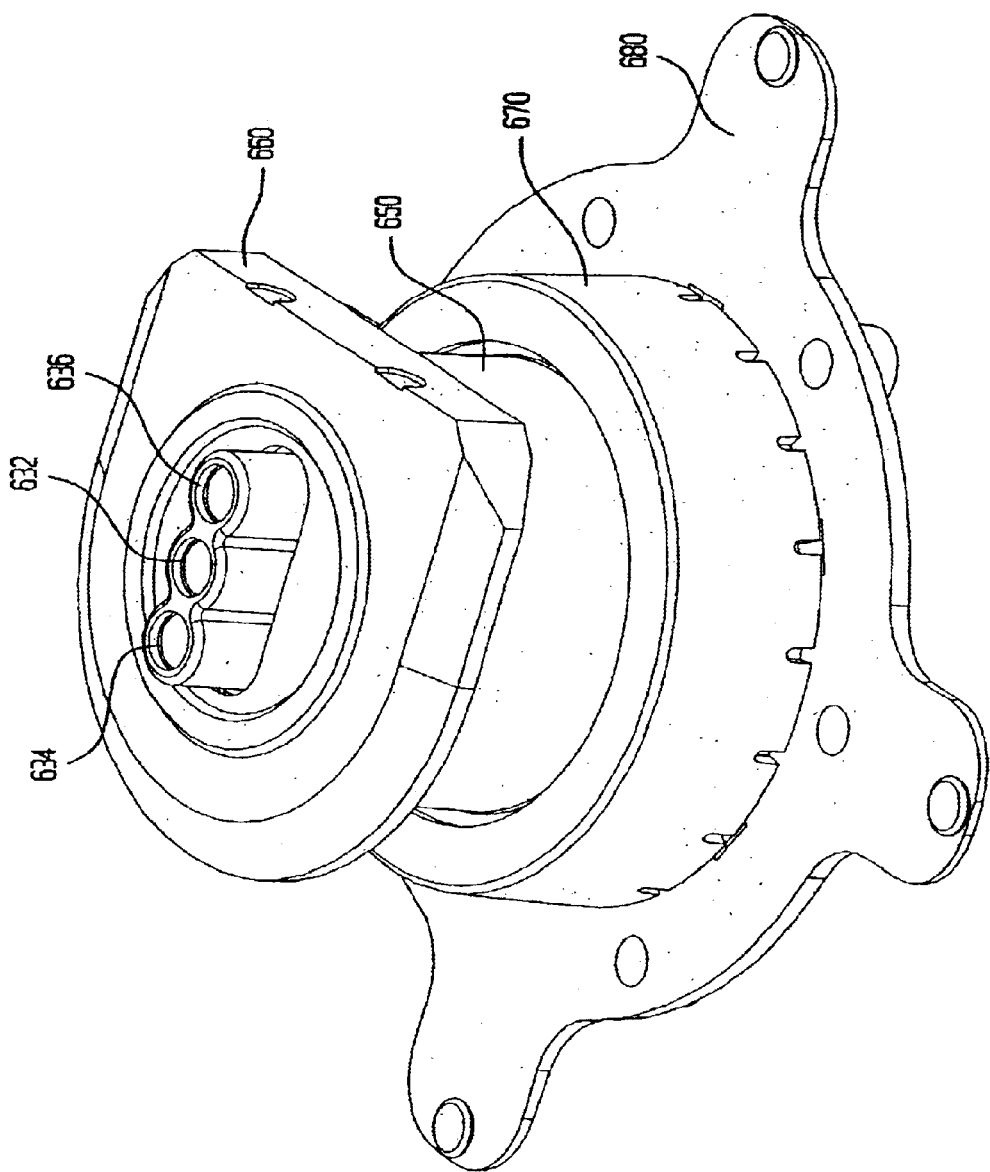
FIG. 15 is an isometric view of the FIG. 14 components in assembled form.
Figure 16:
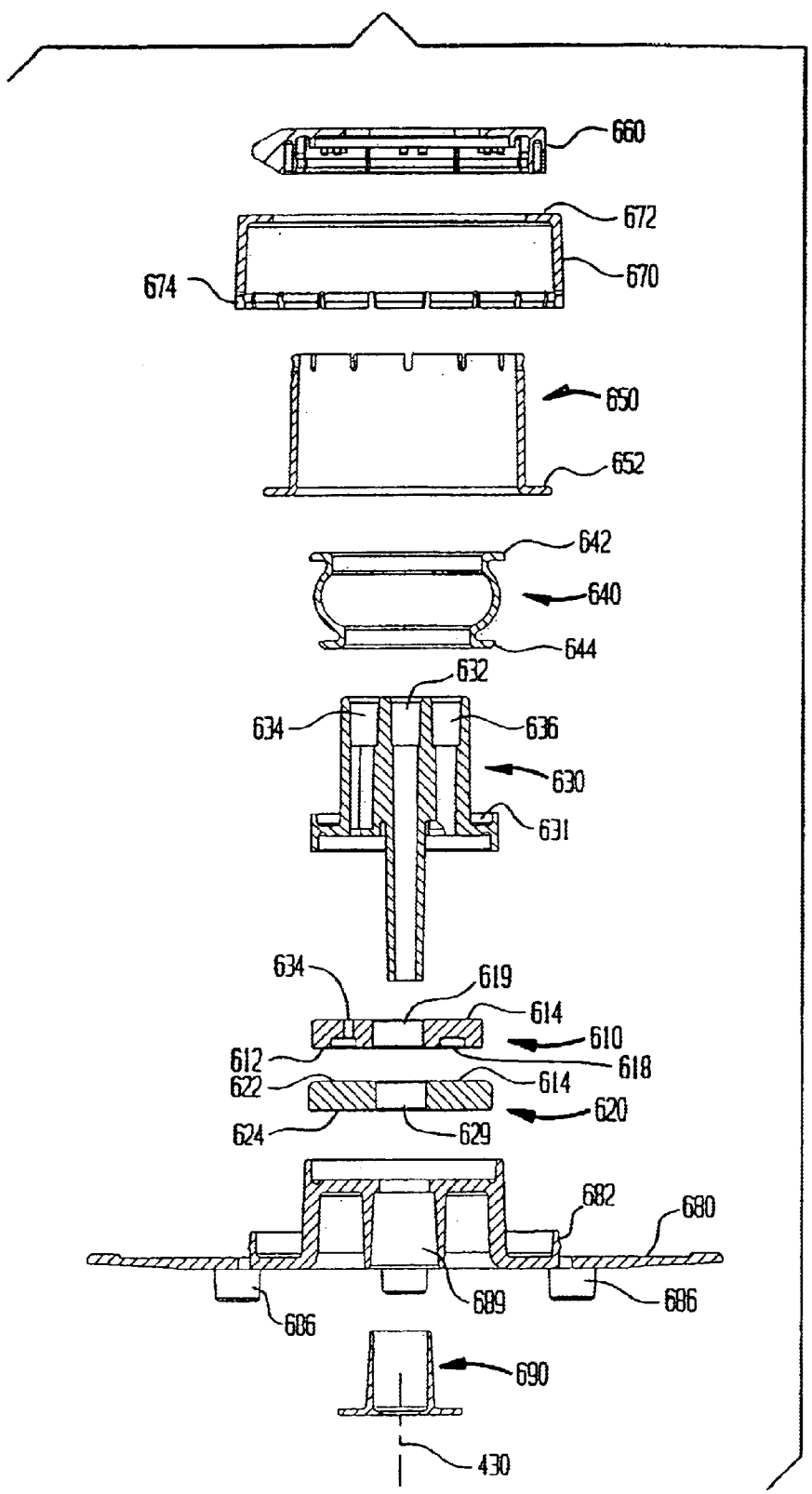
FIG. 16 is an exploded side cross-sectional view of the FIG. 14 rotating seal components.

As shown in FIGS. 5–13, the bucket 404 receives a chuck or rotor 408 which is rotatably drivable around central axis 430 via interconnection to motor 400 through shaft 450 which is housed within bearing housings 451–453 and coupling 452. As shown in FIG. 12, the motor 400 rotatably drives a shaft 455 which is connected to shaft 450 which is connected to chuck 408 which is mounted via grooves 456 and posts 457, FIGS. 7, 8 within the bucket (404) for rotation therein.

As best shown in FIG. 12, expressor fluid is pumped from an external source 425, i.e., external to the rotor, shaft and motor components, into a sealed annular space 458 which communicates with an axial fluid passage 416 through drive shafts 455 and 450. The axial fluid passage 416 communicates with a passage 475 in chuck 408 which communicates with grooves (channels) 410 on the inside surface of chuck 408, FIGS. 5, 6. As best shown in FIG. 6, the fluid delivery grooves 410 extend radially outwardly along a central flat circular surface 460 and further radially outwardly along the curved inside surface of chuck 408.

The grooves (channels) 410 may be formed on a wall of the chuck 408, and may extend from the central axis and end adjacent a circumference of the chuck (for example).

A pair of bearing seals 462, FIG. 12, enable the delivery of fluid from (and to) a stationary source 425 into space 458 and through the axis passage 416 of rotating shafts 455 and 450. Bearings 464, FIG. 12, rotatably mount shaft 450 within housing 451.

The chuck 408 has a round, donut or dish shaped chamber 421, FIGS. 7, 8, 9, 12 within which the separation process occurs. The overall chamber 421 is divided into two separate enclosures, one being the space below flexible membrane 411, and the other being the space within chamber 421 above membrane 411. The space below membrane 411 is sealably enclosed via the sealed mating of the underside of the outside circumference of the membrane with the circumferential rim 409, FIGS. 5, 6 of chuck 408 which is accomplished via the bolting of ring 412 FIGS. 7, 8 to rim 409 with membrane 411 sandwiched therebetween. Membrane 411 is also sealably mated to the central flat surface 460 of chuck 408 via the bolting of chuck plate 413, FIGS. 6, 7 to the center of chuck 408 with the center of membrane 411 sandwiched therebetween, FIGS. 6, 7.

The flexible membrane 411 comprises a resilient stretchable or flexible material typically an elastomeric material such as silicone, urethane or other suitable engineering elastomer such as Eastman Ecdel or DuPont Hytrel. The membrane 411 is non-permeable to fluid or gas and inert and/or non-reactive and/or non-porous to conventional aqueous and organic fluids and biological cells such as blood cells. The membrane 411 material is selected to be a material which stretches and contracts, is resilient, robust, and does not crease or deform upon stretching or contracting.

Figure 5:
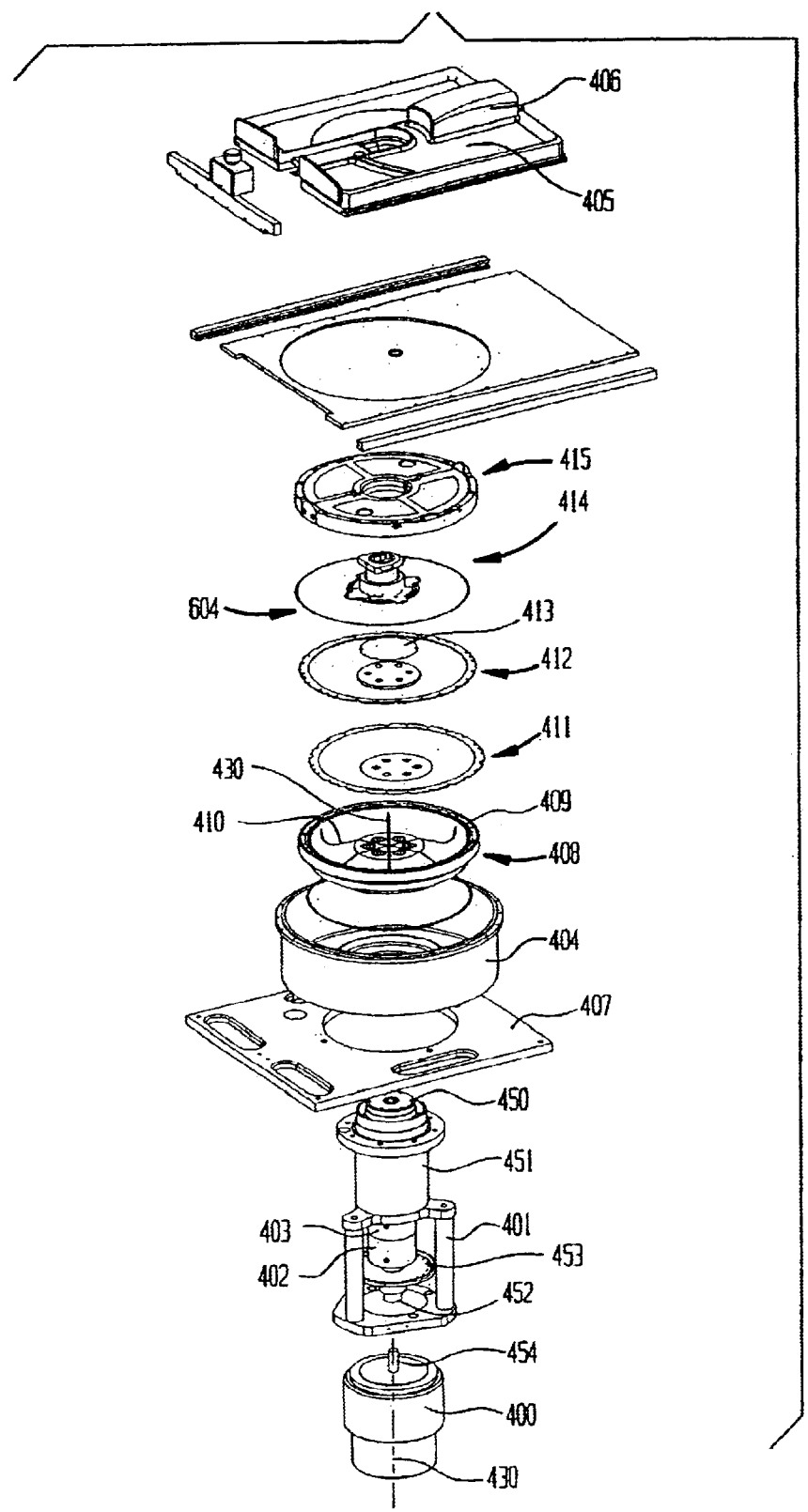
FIG. 5 is an isometric exploded view of components of a subassembly used for expressing selected fluid materials disposed in a flexible container.
Figure 6:
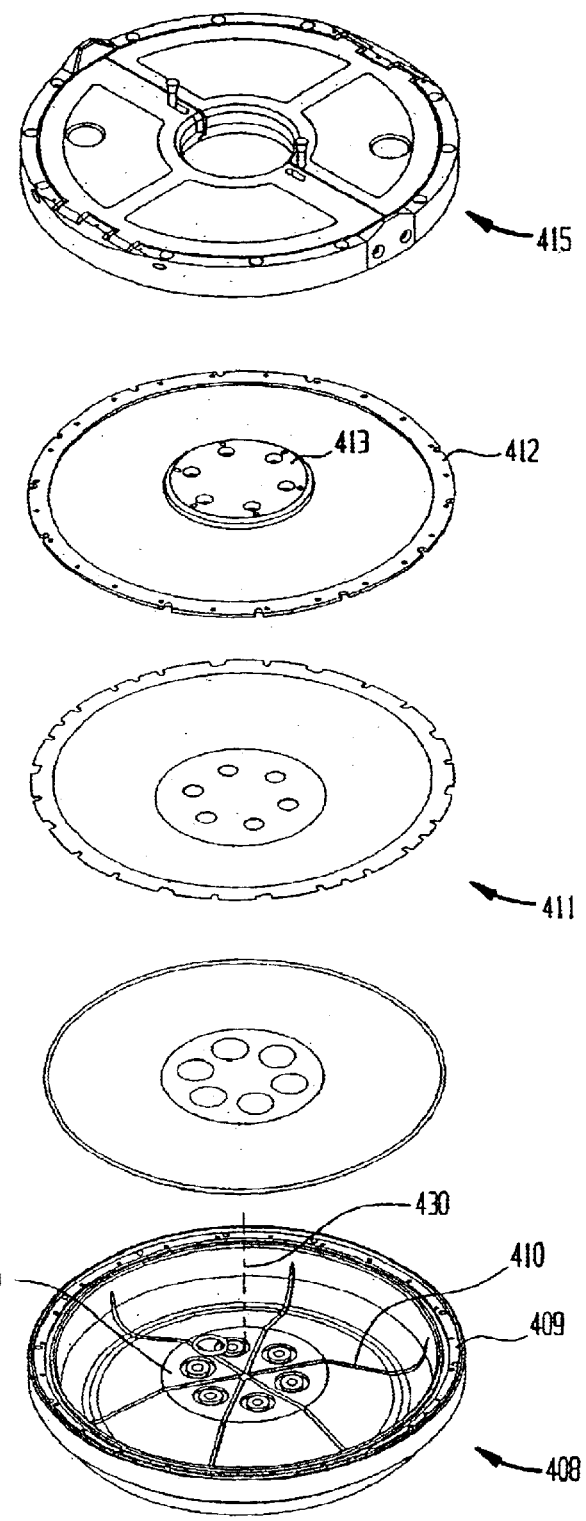
FIG. 6 is an isometric exploded view of certain of the components shown in FIG. 5.
Figure 7:
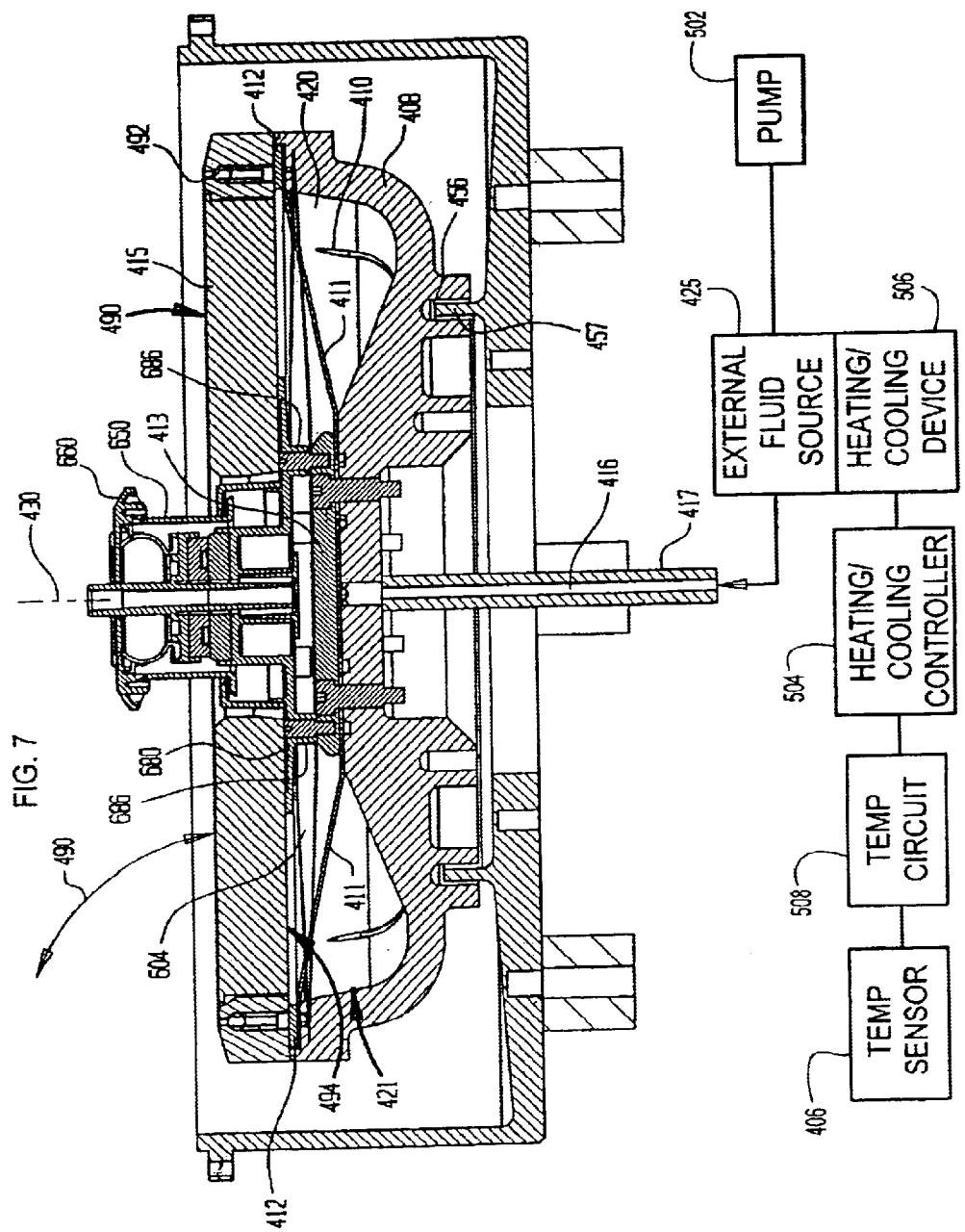
FIG. 7 is a side cross-sectional view of certain components of the expresser system subassembly shown in FIG. 5 taken along one plane which does not intersect one of the fluid flow grooves 410 in chuck 408.
Figure 8:
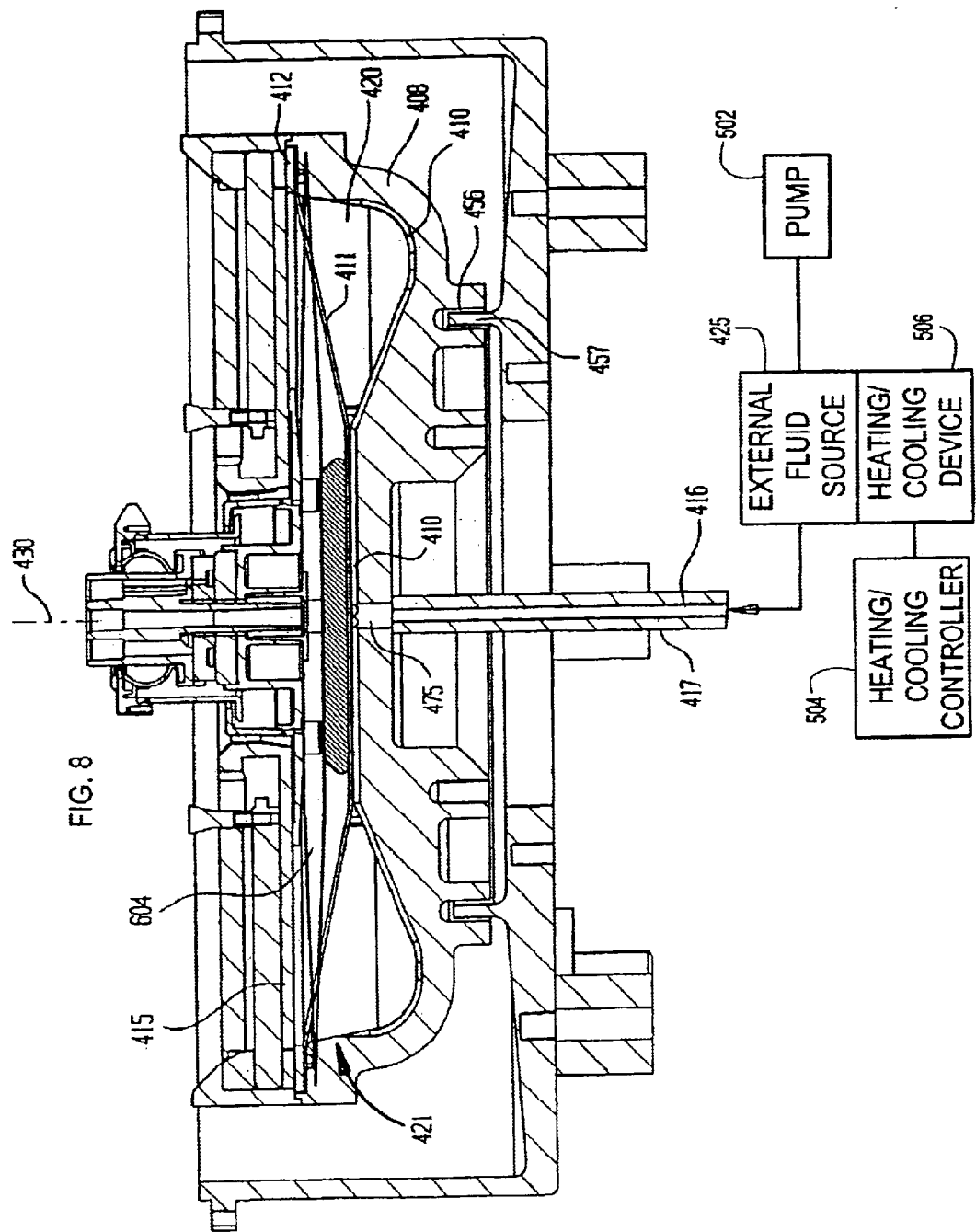
FIG. 8 is another side cross-sectional view of certain components of the expresser system subassembly shown in FIG. 5 taken along a plane which does intersect one of the fluid flow grooves 410 in check 408.

In the chamber space 426 above the top surface of membrane 411 within chamber 421 is mounted round fluid enclosure 604, FIGS. 5, 7, 8 within which one or more fluid materials to be processed in some fashion is/are disposed. The fluid enclosure 604 comprises a flexible material, typically a sheet of plastic which is non-porous and inert to aqueous and biological fluids generally. The plastic material of the fluid enclosure 604 typically comprises polyvinyl chloride (PVC), polyethylene, inert multilayered coextruded plastics such as Cryovac M312, Eastman Ecdel elastomer or other equivalent flexible, inert plastic sheet material. The fluid enclosure 604 typically comprises an enclosure such as a bag (which may be disposable) or another donut shaped enclosure having at least one wall or side comprised of a sheet of the flexible plastic material, the outside surface of which faces the upper/outside surface of membrane 411.

The fluid enclosure 604 is typically filled with two or more fluids, such as an aqueous solution and a collection of biological cells which are to be separated from each other via centrifugal forces or via gravity/sedimentation. For purposes of the present invention, a collection of cells which is capable of flowing relatively smoothly through conventional fluid flow tubing (e.g. having a diameter of at least about 0.10 inches) is considered to be a fluid or fluid material.

Where two or more fluid materials are input into or disposed in the fluid enclosure 604, each fluid material has a different density. The density of any and all materials which are input into or disposed within the fluid enclosure 604 is most preferably selected to be less than the density of the expressor fluid which is selected for input into the expressor space or chamber 420, FIGS. 7–11.

The density of the expressor fluid is preferably selected to be greater than the density of each of the materials disposed in the enclosure 604 so that upon rotation of chuck or rotor 408, the expressor fluid will preferentially travel to the outermost circumference of the chamber 421 under the centrifugal force, as best shown in FIGS. 10, 11 wherein in FIG. 10, a first selected volume of expressor fluid has been pumped into space/enclosure 420 and wherein in FIG. 11, a second greater volume of expressor fluid has been pumped into space/enclosure 420. FIGS. 10, 11 demonstrate that as the volume of the expressor fluid is increased within enclosure 420, during the course of rotation of chuck or rotor 408, the flexible membrane 411 stretches/expands from the outermost circumferential edge of flexible enclosure 604 radially inwardly, thus compressing enclosure 604 radially inwardly and forcing the fluids to flow out of the enclosure 604, through exit port 632, sequentially according to the density of the fluid materials, least dense first to most dense last.

In a typical processing cycle, at the beginning, the membrane 411 is disposed in a position where the membrane 411 is held under suction pressure closely adjacent to the curved inner surface of the processing chamber 421 as shown in FIG. 9. A processing bag/enclosure 604 which, having a fill volume equivalent to space 426, FIG. 9, is filled with a fluid containing biological cells disposed in an aqueous solution containing processing materials such as enzymes or buffers. The filled enclosure 604 is deposited in space 426, FIG. 9, and the enclosure 604 is retained or fixedly held within space 426 via cover plates or doors 415, FIGS. 5–9, which are hingedly attached to chuck or rotor 408. At least the underside 472 of enclosure 604, FIG. 5, comprises a flexible sheet material. The enclosure 604 is positioned within space 426 such that the flexible underside 472 of enclosure 604 faces and/or makes external surface to surface contact with membrane 411 as shown in FIG. 9. Expressor fluid is then controllably pumped from source 425, FIGS. 8,12, into axial channel 416 and flows upwardly to channel space 475 and then, FIG. 8, through grooves 410 into sealed space 420. During the course of pumping the expresser fluid into space 420, the chuck/rotor 408 is typically drivably rotated, the expresser fluid travels to the outermost circumferential volume of the sealed space 420 under centrifugal force, FIG. 10 and the membrane 411 is stretched/expands radially inwardly, FIG. 10, and continues to expand, FIG. 11 radially inwardly. As can be readily imagined as the volume of expressor fluid increases within space 420, FIGS. 10, 11, the bag or enclosure 604 is compressed and the fluids contained within the bag/enclosure 604 are forced radially inwardly to flow out of an exit channel 632 or 636 which are sealably connected to and communicate with the interior space of enclosure 604.

In another embodiment of the invention, relying on gravity force only, the rotor/chuck 408 may not necessarily be rotated during input/pumping in of the expressor fluid. In such an embodiment, the expressor fluid may fill the sealed expresser space 420 from the gravitational bottom of the chamber 421 and expand the space 420 from the bottom upwardly compressing the bag/enclosure 604 from the bottom upwardly. Because the two or more materials disposed within the bag/enclosure 604 have different densities, the two or more materials will separate from each other within the bag/enclosure 604 over a certain period of time (depending on the densities of the fluid materials) under the force of gravity. Once the materials have been allowed to separate over time, the expressor fluid may be pumped into space 420 and the gravitationally separated materials may be compressed out of an exit channel 632, 636 sequentially according to their densities, least dense first to most dense last.

The expressor fluid is preferably selected to have a lubricating effect on the rotating bearing seals 462, FIG. 12, and selected to be non-corrosive and not overly viscous. Most preferably the expressor fluid is a mixture of glycerine and ethylene glycol in a ratio of between about 40:60 and about 60:40, most preferably about 50:50 (having a density of about 1.15) which, for the vast majority of biological fluid applications, has a density greater than the density of the biological fluids. Other examples of expresser fluids having a density greater than most biological fluids are glycerol and ethylene glycol diacetate which are less preferred. Any stable, non-corrosive, relatively non-viscous fluid preferably having a density greater than the density of each of the fluid materials disposed in the enclosure 604 may be used as an expressor fluid.

The enclosure 604 which receives the fluids to be processed is a sealed enclosure, preferably having a fluid input port 632, 636 which is/are readily sealably attachable to a readily selectable source of fluid, such as wash or preservative or compacting fluid or buffer or biological cell containing or enzyme containing fluid. Such selectable sources of input fluids may be each connected to a manifold or fluid management apparatus (e.g. a subassembly or subsystem of module 40, FIG. 1) which can be programmed or otherwise readily controlled to deliver a selected fluid for input to the enclosure 604. An output port of such a manifold or fluid management apparatus is readily sealably connectable to an input port 632, 636 of the enclosure 604.

In the embodiment shown in FIGS. 9, 14, 15, 16, several fluid communication ports 632, 636 are provided, each port being both an input and an exit/output port. In the specific embodiment shown, one fluid communication port 632 may be utilized for inputting and outputting a biological cell material and the other port 636 might be utilized for inputting/outputting a processing fluid (e.g. buffer or enzyme containing aqueous solution). The ports 632, 636 may be sealably connected to a fluid management apparatus as discussed with reference to FIG. 1, wherein a series of valves are utilized to separately enable flow into, out of or through one port or another at any given time. The input/output ports 632, 636 of the enclosure 604 sealably communicate with the interior of enclosure 604 via the assembly and fastening together of rotating seal components 630 (body), 610 (upper seal), 620 (lower seal), 670 (header clamp), 680 (base), 681 (plug), FIGS. 14–16 together with bag/enclosure 604 so as to provide several sealed fluid communication ports 632, 636 into and out of the interior 426 of the enclosure 604, FIG. 9. Another channel 634 as shown is provided in the rotating seal components 630 and 610, FIGS. 14, 16 for input of sterile gas between and around the undersurface 612 and upper surface 622 of seal components 610, 620 which mate and rotate with respect to each other.

Most preferably, when biological cells are input into enclosure 604 together with a selected processing fluid having a predetermined composition, the ratio of the amount of biological cells and processing fluid is maintained constant between any two or more processing cycles, i.e., the processing conditions to which any two separate aliquots of biological cells are subjected is identical as between separate processing cycles.

As can be readily imagined, the volume of fluid input into the processing enclosure 604 at the beginning of any particular processing cycle may be selectively varied, (i.e., the processing enclosure 604 may be filled anywhere from 0–100% of its volume capacity), with the remaining unoccupied volume of the processing chamber 421 being selectively filled up by inputting or pumping in an appropriate amount of expresser fluid into enclosure 420. Most preferably, the maximum volume or capacity of the processing enclosure 604 is approximately equal to or slightly less than the volume of the chamber 421. As described above, the hinged doors 415 are pivotable 490, FIG. 7 between open and closed positions, the doors 415 being shown in the closed position in FIGS. 7–9. When the doors are opened, the bag enclosure 604 is insertable into chamber 421 and when the doors are closed as shown in FIG. 7–9, the bag/enclosure 604 is firmly held within the volume of chamber 421. The doors are lockable into the closed position shown in FIGS. 7–9 by conventional means such as via spring based hinges 492 or other conventional means such as clasps, clamps or the like. The undersurface 494 of door retains the bag/enclosure 604 within chamber 421 and provides a stationary surface against which the bag/enclosure 604 engages and thereby is forced to compress under the opposing pressure exerted by the flexible membrane 411 on the flexible wall of the bag/enclosure 604 when the space 420 is expanding as described for example above the reference to FIGS. 10, 11. Suitable alternative mechanisms to doors 415 may comprise, for example, a plate or disc which is slidable into a stationary position equivalent to the closed position of doors 415, FIGS. 7–9.

The apparatus includes a sensor for monitoring the temperature of the fluids disposed in the processing enclosure 604. In a preferred embodiment, the temperature sensor comprises an infrared IR thermocouple 406, FIG. 5, which detects IR radiation in a range of about 2 $\mu$m to 10 $\mu$m emitted through an IR transparent window disposed over the bag/enclosure 604. The transparent window typically comprises ZnSe and is coated by a 0.5 mill layer of parylene N. The parylene N coating is used to protect the transparent window although it has some absorption of the IR radiation. Other conventional temperature sensors may also be employed.

In the disclosed embodiment, the IR thermocouple (e.g. IR t/c.03-J-80F/27C may be Exergen, Corp., 51 Water Street, Watertown, Mass. 02172) integrates the detected IR energy to determine the temperature of the fluids. This temperature is corrected for the local air temperature or ambient temperature between the transparent window and processing enclosure 604. This air temperature is measured by a second temperature sensor that is a Si diode temperature sensor. The data from the Si diode is used for correcting the IR data.

Most preferably, the temperature of the fluids disposed in the processing enclosure 604 is controlled by controlling the temperature of the expresser fluid which is input into the expresser chamber/space 420. Preferably, the source of expresser fluid 425, FIGS. 7–9, 12 which is pumped via pump 502 into annular space 458, FIG. 12 and through channel 416 and ultimately into chamber space 420, is connected to a fluid heating and/or cooling device 506, FIGS. 7–9, 12 which is controlled by a heating and/or cooling controller 504. The expresser fluid is typically circulated through a reservoir, within which, the fluid is in thermal contact with certain devices that transfer thermal energy to or from the fluid in response to a control algorithm. These thermal devices may include Peltier Devices, electric resistance submersion heaters, air cooled radiators, or other similar devices or some combination of these types of thermal transfer devices. The expresser fluid which travels through channel 416 and grooves 410 makes contact with the surfaces of rotor or chuck 408 and the membrane 411 and the shafts 450, 455. Rotor 408 and shafts 450, 455 are typically comprised of a heat conductive material such as metal (e.g. steel, iron, copper, aluminum or the like) and are thus readily heated or cooled to the temperature of the expresser fluid with which they are in contact. The temperature of the expresser fluid is thus readily conducted to the fluids disposed in the processing bag/enclosure 604 via the rotor 408, shafts 450, 455 and through the flexible membrane 411 with which the flexible wall of the bag/enclosure 604 makes contact within chamber 421. Thus, by controlling the temperature of the external source 425 of expresser fluid, the temperature of the entire processing system, including the interior chamber 421, may be controlled.

The temperature of the fluid being monitored by sensor 406 may be input to a program or circuit 508 connected to controller 504, FIGS. 4, 7–9, 12. The program or circuit 508 preferably includes a subroutine for automatically directing the temperature controller to heat or cool the temperature of the expresser fluid source 425 to a predetermined constant temperature or series of temperatures over a predetermined period of time. The program 508 preferably includes a predetermined algorithm which uses the temperature information signal which is input from sensor 406 to direct control of the temperature controller 504 and heater and/or cooler element 506 such that the temperature of the external source 425 of expresser fluid is varied depending on the temperature signal input from sensor 406. In one embodiment of the invention, the temperature of the source 425 may be cooled by simply terminating heating of the expresser fluid 425 thus allowing the fluids 425 to passively cool by self-radiation of heat rather than by proactive cooling.

What is claimed is:

1. An apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising:
   a centrifuge rotor having a round centrifuge chamber of selected volume and a channel provided on a wall of the chamber extending from a central axis and ending adjacent a circumference of the rotor, wherein the centrifuge rotor being controllably rotatable around the central axis by a motor mechanism;
   a round expandable enclosure disposed within the centrifuge chamber having a rotation axis coincident with the central rotation axis and a flexible wall, the fluid container having a rotation axis and being coaxially receivable within the centrifuge chamber, the expandable enclosure being sealably connected to a source of an expresser fluid which has a density selected to be greater than the density of each of the selected one or more fluid materials disposed in the fluid container;
   a pump for controllably pumping a selected volume of the expresser fluid into and out of the expandable enclosure wherein the fluid container is receivable within the centrifuge chamber; and
   a retaining mechanism for holding the fluid container within the centrifuge chamber in a coaxial position wherein the flexible wall of the fluid container is in contact with the flexible wall of the expandable enclosure.

2. The apparatus of claim 1 wherein the expandable enclosure comprises a flexible membrane sealably attached to a surface of the rotor such that the centrifuge chamber is divided into a first chamber for receiving the fluid container and a second fluid sealed chamber for receiving the expresser fluid.

3. The apparatus of claim 1 wherein the flexible wall of the expandable enclosure comprises an elastromeric sheet material.

4. The apparatus of claim 1 further comprising a heater mechanism having a control mechanism for selectively controlling the temperature of the expresser fluid.

5. The apparatus of claim 1 wherein the fluid container has a first radius and the second fluid sealed chamber has a second radius which is at least equal to the first radius of the fluid container, wherein the expresser fluid pumped into the second fluid sealed chamber travels to a circumferential position within the second fluid sealed chamber which is more radially outward from the central axis than a circumferential position to which the one or more selected fluid materials in the fluid container travel when the rotor is drivably rotated around the central axis.

6. Apparatus of claim 1 further comprising a temperature sensor connected to a program, wherein the temperature of the fluid materials is sensed by the temperature sensor, the program being connected to a temperature mechanism which controls the temperature of the expresser fluid.

7. An apparatus for selectively expressing one or more selected fluid materials out of a fluid container, wherein each of the selected fluid materials has a selected density and wherein the fluid container comprises a round enclosure having a rotation axis, a flexible wall and an exit port sealably communicating with the container for enabling the selected fluid materials contained therein to be expressed out of the container through the exit port, the apparatus comprising:
   a centrifuge rotor having a round centrifuge chamber and a channel provided on a wall of the chamber extending from a central axis and ending adjacent a circumference of the chamber, the centrifuge rotor being controllably rotatable around a central axis by a motor mechanism;
   a flexible membrane sealable attached to a surface of the rotor such that the centrifuge chamber is divided into a first chamber for receiving the fluid container coaxially with the central rotation axis and a second round fluid sealed chamber having a rotation axis coincident with the central axis for receiving an expresser fluid, wherein the expresser fluid has a density selected to be greater than the density of each of the selected one or more fluid materials disposed in the container;
   a pump for controllably pumping a selected volume of the expresser fluid into and out of the second fluid sealed centrifuge chamber; and
   a retaining mechanism for holding the container within the first chamber in a position wherein the flexible wall of the container is in contact with an outside surface of the flexible membrane.

8. The apparatus of claim 7 wherein the flexible membrane comprises an elastomeric sheet material.

9. The apparatus of claim 7 further comprising a heater mechanism having a control mechanism for selectively controlling the temperature of the expresser fluid.

10. The apparatus of claim 7 wherein the fluid container has a first radius and the second fluid sealed chamber has a second radius which is at least equal to the first radius of the fluid container, wherein the expresser fluid pumped into the second fluid sealed chamber travels to a circumferential position within the second fluid sealed chamber which is more radially outward from the central axis than a circumferential position to which the one or more selected fluid materials in the fluid container travel when the rotor is drivably rotated around the central axis.

11. Apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising:
   a separation housing having a round chamber of selected volume, the housing having a central axis and the round chamber including a wall having a channel positioned thereon extending from the central axis and ending adjacent a circumference of the round chamber;
   a round expandable enclosure disposed within the round chamber having an axis coincident with the central axis of the separation chamber and a flexible wall, the fluid container having an axis and being coaxially receivable within the round chamber, the expandable enclosure being sealably connected to a source of an expresser fluid which has a density selected to be greater than the density of each of the selected one or more fluid materials disposed in the fluid container;
   a pump for controllably pumping a selected volume of the expresser fluid into and out of the expandable enclosure wherein the fluid container is receivable within the round chamber; and a retaining mechanism for holding the fluid container within the round chamber in a coaxial position wherein the flexible wall of the fluid container is in contact with the flexible wall of the expandable enclosure.

12. The apparatus of claim 11 wherein the expandable enclosure comprises a flexible membrane sealably to a surface of the separation housing such that the round chamber is divided into a first chamber for receiving the fluid container and a second fluid sealed chamber for receiving the expresser fluid.

13. The apparatus of claim 11 wherein the flexible wall of the expandable enclosure comprises an elastomeric sheet material.

14. The apparatus of claim 11 wherein the fluid container has a first radius and the expandable enclosure has a second radius which is at least equal to the first radius of the fluid container.

15. The apparatus of claim 11 further comprising a heater mechanism having a control mechanism for selectively controlling the temperature of the expresser fluid.

16. An apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising:

a centrifuge rotor having a round centrifuge chamber of selected volume and having a channel positioned on a wall of the chamber extending from a central axis and ending adjacent a circumference of the chamber, the centrifuge rotor being controllable rotable around a central axis by a motor mechanism;

a round expandable enclosure disposed within the centrifuge chamber having a rotation axis coincident with the central rotation axis and a flexible wall, the fluid container having a rotation axis and being coaxially receivable with the centrifuge chamber, the expandable enclosure being sealably connected to a source of an expresser fluid;

a pump for controllably pumping a selected volume of the expresser fluid into an out of the expandable enclosure;

wherein the fluid container has a flexible wall and is receivable within the centrifuge chamber such that the flexible wall of the fluid container faces the flexible wall of the expandable enclosure;

a mechanism for filling the fluid container with any preselected variable volume of the one or more selected fluid materials which is less than the selected volume of the centrifuge chamber; and a retaining mechanism for holding the fluid container completely within the centrifuge chamber upon expansion of the expandable enclosure.

17. The apparatus of claim 16 wherein the expandable enclosure comprises a flexible membrane sealably attached to a surface of the rotor such that the centrifuge chamber is divided into a first chamber for receiving the fluid container and a second fluid sealed chamber for receiving the expresser fluid.

18. The apparatus of claim 16 wherein the flexible wall of the expandable enclosure comprises an elastomeric sheet material.

19. The apparatus of claim 16 wherein the expresser fluid has a density selected to be greater than the density of each of the selected one or more fluid materials disposed in the fluid container.

20. The apparatus of claim 16 wherein the fluid container has a first radius and the expandable enclosure has a second radius which is at least equal to the first radius of the fluid container, wherein the expresser fluid pumped into the expandable enclosure travels to a circumferential position within the expandable enclosure which is more radially outward from the central axis than a circumferential position to which the one or more selected fluid materials in the fluid container travel when the rotor is drivably rotated around the central axis.

21. The apparatus of claim 16 further comprising a heater mechanism having a control mechanism for selectively controlling the temperature of the expresser fluid.

22. Apparatus for selectively expressing one or more selected fluid materials out of a fluid container, wherein each of the selected fluid materials has a selected density and wherein the fluid container comprises a round enclosure having a rotation axis, a flexible wall and an exit port sealably communicating with the container for enabling the selected fluid materials contained therein to be expressed out of the container through the exit port, the apparatus comprising:

a centrifuge rotor having a round centrifuge chamber of selected volume and a channel provided thereon, wherein the channel extends from a central axis and ends adjacent a circumference of the rotor and wherein the centrifuge rotor is controllably rotatable around the central axis by a motor mechanism;

a flexible membrane sealably attached to a surface of the rotor such that the centrifuge chamber is divided into a first chamber for receiving the fluid container coaxially with the central rotation axis and a second round fluid sealed chamber having a rotation axis coincident with the central axis for receiving the expressor fluid;

a pump for controllably pumping a selected volume of the expressor fluid into and out of the second fluid sealed centrifuge chamber, wherein the fluid container has a flexible wall and is receivable within the centrifuge chamber such that the flexible wall of the fluid container faces the flexible wall of the expandable enclosure;

a mechanism for filling the fluid container with any preselected variable volume of the one more selected fluid materials which is less than the selected volume of the centrifuge chamber; and a retaining mechanism for holding the fluid container completely within the centrifuge chamber upon expansion of the expandable enclosure.

23. The apparatus of claim 22 wherein the flexible membrane comprises an elastomeric sheet material.

24. The apparatus of claim 22 wherein the expresser fluid has a density selected to be greater than the density of each of the selected one or more fluid materials disposed in the fluid container.

25. The apparatus of claim 22 wherein the fluid container has a first radius and the second fluid sealed chamber has a second radius which is at least equal to the first radius of the fluid container, wherein the expresser fluid pumped into the second fluid sealed chamber travels to a circumferential position within the second fluid sealed chamber which is more radially outward from the central axis than a circumferential position to which the one or more selected fluid materials in the fluid container travel when the rotor is drivably rotated around the central axis.

26. The apparatus of claim 22 further comprising a heater mechanism having a control mechanism for selectively controlling the temperature of the expresser fluid.

27. Apparatus for selectively expressing one or more selected fluid materials out of a fluid container, wherein each of the selected fluid materials has a selected density and wherein the fluid container comprises a round enclosure having a flexible wall and an exit port sealably communicating with the fluid container for enabling the selected fluid materials contained therein to be expressed out of the fluid container through the exit port, the apparatus comprising:

a centrifuge rotor having a round centrifuge chamber of selected volume and a channel provided thereon, wherein the channel extends from a central axis of the chamber and ends adjacent a circumference of the chamber and wherein the centrifuge rotor is controllably rotatable around the central axis by a motor mechanism;

a round expandable enclosure disposed within the centrifuge chamber having a rotation axis coincident with the central axis and a flexible wall, the fluid container having a rotation axis and being coaxially receivable within the centrifuge chamber, the expandable enclosure being sealably connected to a source of the expressor fluid;

a pump for controllably pumping a selected volume of the expresser fluid into and out of the expandable enclosure wherein the fluid container is receivable within the centrifuge chamber;

a heater mechanism having a control mechanism for selectively controlling the temperature of the expressor fluid; and a retaining mechanism for holding the fluid container within the first chamber in a coaxial position wherein the flexible wall of the fluid container is in contact with the flexible wall of the fluid container.

28. The apparatus of claim 27 wherein the control mechanism includes a program for automatically controlling the temperature of the expresser fluid.

29. The apparatus of claim 27 wherein the expandable enclosure comprises a flexible membrane sealably attached to a surface of the rotor such that the centrifuge chamber is divided into a first chamber for receiving the fluid container and a second fluid sealed chamber for receiving the expresser fluid.

30. The apparatus of claim 27 wherein the flexible wall of the expandable enclosure comprises an elastomeric sheet material.

31. The apparatus of claim 27 wherein the expresser fluid has a density selected to be greater than the density of each of the selected one or more fluid materials disposed in the container.

32. The apparatus of claim 27 wherein the fluid container has a first radius and the second fluid sealed chamber has a second radius which is at least equal to the first radius of the fluid container, wherein the expresser fluid pumped into the second fluid sealed chamber travels to a circumferential position within the second fluid sealed chamber which is more radially outward from the central axis than a circumferential position to which the one or more selected fluid materials in the fluid container travel when the rotor is drivably rotated around the central axis.

33. Apparatus for selectively expressing one or more selected fluid materials out of a fluid container, wherein each of the selected fluid materials has a selected density and wherein the fluid container comprises a round enclosure having a rotation axis, a flexible wall and an exit port sealably communicating with the container for enabling the selected fluid materials contained therein to be expressed out of the container through the exit port, the apparatus comprising:

a centrifuge rotor having a round centrifuge chamber of selected volume and a channel provided thereon wherein the channel extends from a central axis and ends adjacent a circumference of the rotor and wherein the centrifuge rotor is controllably rotatable around the central axis by a motor mechanism;

a flexible membrane sealably attached to a surface of the rotor such that the centrifuge chamber is divided into a first chamber for receiving the fluid container coaxially with the central rotation axis and a second round fluid sealed chamber having a rotation axis coincident with the central axis for receiving an expressor fluid;

a pump for controllably pumping a selected volume of the expresser fluid into and out of the second fluid sealed centrifuge chamber;

a heater mechanism having a control mechanism for selectively controlling the temperature of the expressor fluid; and a retaining mechanism for holding the container within the first chamber in a position wherein the flexible wall of the container is in contact with an outside surface of the flexible membrane.

34. The apparatus of claim 33 wherein the control mechanism includes a program for automatically controlling the temperature of the expresser fluid.

35. The apparatus of claim 33 wherein the flexible membrane comprises an elastomeric sheet material.

36. The apparatus of claim 33 wherein the expresser fluid has a density selected to be greater than the density of each of the selected one or more fluid materials disposed in the container.

37. The apparatus of claim 33 wherein the fluid container has a first radius and the second fluid sealed chamber has a second radius which is at least equal to the first radius of the fluid container, wherein the expresser fluid pumped into the second fluid sealed chamber travels to a circumferential position within the second fluid sealed chamber which is more radially outward from the central axis than a circumferential position to which the one or more selected fluid materials in the fluid container travel when the rotor is drivably rotated around the central axis.

\* \* \* \* \*

UNITED STATES PATENT AND TRADEMARK OFFICE
CERTIFICATE OF CORRECTION

PATENT NO. : 6,852,074 B1
DATED : February 8, 2005
INVENTOR(S) : Glen Jorgensen et al.

It is certified that error appears in the above-identified patent and that said Letters Patent is hereby corrected as shown below:

<u>Title page,</u>
Items [12] and [75], should read as follows:
-- [12] United States Patent
      Jorgensen et al.

[75] Inventors:    Glen Jorgensen --

Signed and Sealed this

Twenty-sixth Day of April, 2005

JON W. DUDAS
*Director of the United States Patent and Trademark Office*